United States Patent [19]

Ooms et al.

[11] Patent Number: 4,874,766

[45] Date of Patent: Oct. 17, 1989

[54] METHOD OF PROMOTING WOUND-HEALING

[75] Inventors: Leo A. A. Ooms, Wechelderzande; Anne-Dominique A. Y. Degryse, Herentals, both of Belgium

[73] Assignee: Janssen Pharmaceutica N.V., Beerse, Belgium

[21] Appl. No.: 88,444

[22] Filed: Aug. 24, 1987

Related U.S. Application Data

[63] Continuation-in-part of Ser. No. 909,991, Sep. 22, 1986, abandoned.

[51] Int. Cl.$^4$ ............................................. A61K 31/505
[52] U.S. Cl. ..................................... 514/258; 514/259
[58] Field of Search ................................ 514/258, 259

[56] References Cited

U.S. PATENT DOCUMENTS

| | | | |
|---|---|---|---|
| 3,218,324 | 11/1965 | Hofmann et al. | ............... 514/929 X |
| 4,335,127 | 6/1982 | Vanderderk et al. | ............... 514/259 |
| 4,485,107 | 11/1984 | Kennis et al. | ............... 514/269 |

*Primary Examiner*—Leonard Schenkman

[57] ABSTRACT

Method of promoting wound-healing by topically applying a serotonin-antagonistic compound.

17 Claims, No Drawings

METHOD OF PROMOTING WOUND-HEALING

This application is a continuation-in-part of U.S. Ser. No. 909,991 filed Sept. 22, 1986, now abandoned.

BACKGROUND OF THE INVENTION

A rapid and smooth healing of wounds of various nature is generally considered an important goal to achieve. This is mainly due to the fact that the risk of infections and of concomittant complications tends to increase with the duration and complexity of the healing process.

Up until now, quite a number of preparations have been developed to improve the wound-healing process, said preparations containing various active ingredients such as, for example, disinfectants, antibiotics, anti-inflammatory agents, etc..

Quite unexpectedly, it now has been found that the topical treatment of wounds with agents having serotonin-antagonistic properties enhances and improves the wound-healing process.

DESCRIPTION OF THE INVENTION

The present invention is concerned with a method of treating wounds in order to promote the healing process by topically applying to said wounds a compound having serotin-antagonistic properties.

As serotonin-antagonists there may be mentioned the compounds described in U.S. Pat. Nos. 3,272,826 (e.g. pizotifen), 3,014,911 (e.g. cyproheptadine), 3,534,041 (e.g. mianserin), 3,238,211 (e.g. metergolide), 3,218,324 (e.g. methysergide), 3,201,401 (e.g. cinanserin), 3,041,344 (e.g. pipamperone), 3,238,216 (e.g. spiperone), all incorporated herewith by reference, and the like serotonin-antagonists.

In particular, said compound is selected among the serotonin-antagonistic compounds described in U.S. Pat. Nos. 4,335,127, 4,342,870, 4,443,451, 4,485,107 and in the Published Eur. Pat. Appl. No. 0,184,258, all incorporated herewith by reference, and is more preferably selected from the group consisting of those compounds being represented by the general formula

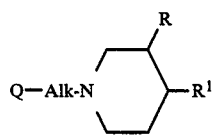

the pharmaceutically acceptable acid-addition salts thereof and the possible stereoisomeric forms thereof; wherein R is hydrogen or $C_{1-6}$alkyl;
Alk is $C_{1-4}$alkanediyl;
Q is a radical of formula

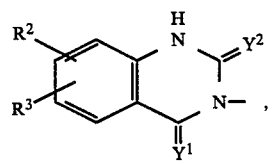

wherein
$Y^1$ and $Y^2$ are each independently O or S;
$R^2$ is hydrogen, halo, $C_{1-6}$alkyl, $C_{1-6}$alkyloxy, $CF_3$, $NO_2$, cyano, hydroxy, ($C_{1-10}$alkylcarbonyl)oxy, amino, mono- and di($C_{1-6}$alkyl)amino, ($C_{1-10}$alkylcarbonyl)amino, phenylmethoxy or azido;
$R^3$ is hydrogen or halo; or
Q is a radical of formula

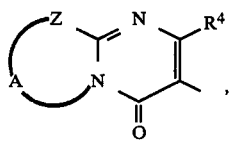

wherein
$R^4$ is hydrogen or $C_{1-6}$alkyl;
Z is —S—, —$CH_2$— or —$CR^5$=$CR^6$—; said $R^5$ and $R^6$ being each independently hydrogen or $C_{1-6}$alkyl; and
A is a bivalent radical —$CH_2$—$CH_2$—, —$CH_2$—$CH_2$—$CH_2$— or —$CR^7$=$CR^8$—, said $R^7$ and $R^8$ being each independently hydrogen, halo, amino or $C_{1-6}$alkyl;
$R^1$ is a radical of formula —X—Ar (c), wherein
Ar is phenyl or substituted phenyl, said substituted phenyl bearing an amino group and/or 1, 2 or 3 halo atoms; and
wherein
X is $>C=O$, $>CH-OH$, $>CH-O-C(O)-R^9$, $>CH_2$, $>C(OC_{1-6}alkyl)_2$, $>C\underset{O}{\overset{O}{<}}(CH_2)_q$, $>C=N-OH$ or $>C=N-NH_2$;

said $R^9$ being hydrogen or $C_{1-6}$ alkyl and
said q being the integer 2 or 3; or
$R^1$ is a radical of formula

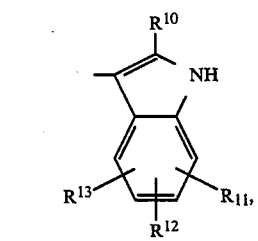

wherein
$R^{10}$ is hydrogen or $C_{1-6}$alkyl; $R^{11}$, $R^{12}$ and $R^{13}$ are each independently hydrogen or halo;
or
$R^1$ is a radical of formula

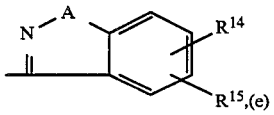

wherein

A is O or S; $R^{14}$ and $R^{15}$ are each independently hydrogen, halo, hydroxy, $C_{1-6}$alkyloxy or $C_{1-6}$alkyl.

As used in the foregoing definitions the term halo is generic to fluoro, chloro, bromo and iodo; the term "$C_{1-6}$alkyl" is meant to include straight and branch chained saturated hydrocarbon radicals having from 1 to 6 carbon atoms such as, for example, methyl, ethyl, 1-methylethyl, 1,1-dimethylethyl, propyl, 2-methylpropyl, butyl, pentyl, hexyl and the like; "$C_{1-10}$alkyl" is meant to include $C_{1-6}$alkyl radicals, as defined hereinabove, and the higher homologs thereof having from 7 to 10 carbon atoms; and "$C_{1-4}$alkanediyl" is meant to include bivalent straight or branch chained alkanediyl radicals having from 1 to 4 carbon atoms.

Preferred compounds of formula (I) to be used in the method of the present invention are those wherein $R^1$ is a radical of formula (c).

Particularly preferred compounds of formula (I) to be used in the method of the present invention are those preferred compounds of formula (I) wherein Q is a radical of formula (a) wherein $Y^1$ and $Y^2$ are both oxygen atoms and $R^2$ and $R^3$ are both hydrogen; or wherein Q is a radical of formula (b), wherein $R^4$ is methyl, Z is —$CR^5$=$CR^6$— wherein $R^5$ and $R^6$ are independently hydrogen or methyl, A is —$CR^7$=$CR^8$— wherein $R^7$ and $R^8$ are independently hydrogen or methyl; and wherein in the radical (c) X is

and Ar is halo substituted phenyl.

The most preferred compounds to be used in the method of the present invention are selected from the group consisting of 3-[2-[4-(4-fluorobenzoyl)-1-piperidinyl]ethyl]-2,4(1H, 3H)-quinazolinedione which compound is generically designated as ketanserin, and 3-[2-[4-(4-fluorobenzoyl)-1-piperidinyl]ethyl]-2,7-dimethyl-4H-pyrido-[1,2-a]pyrimidin-4-one and the pharmaceutically acceptable acid-addition salts thereof.

The compounds of formula (I) can be used as such or in their acid-addition salt form. The latter can conveniently be obtained by treating the base-form with appropriate acids, such as, for example, inorganic acid, such as hydrohalic acid, e.g. hydrochloric, hydrobromic and the like, and sulfuric acid, nitric acid, phosphoric acid and the like; or organic acids, such as, for example, acetic, propanoic, hydroxyacetic, 2-hydroxypropanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids.

The compounds of formula (I) preferably used in the method of the present invention are known serotonin antagonists and their preparation as well as their pharmacological properties have been described in U.S. Pat. Nos. 4,335,127, 4,342,870, 4,443,451 and in the Published Eur. Pat. Appl. No. 0,184,258.

The serotonin-antagonistic compounds used in the method of the present invention are most preferably applied in the form of appropriate compositions, in particular compositions usually employed for topically administering drugs. Said compositions may take a wide variety of forms such as, for example, solid forms, e.g. powders; liquid forms, e.g. solutions or suspensions in aqueous or oily mediums; semi-liquid formulations, e.g. creams, gellies, pastes, ointments, salves. Said compositions contain the active ingredient and a wound-acceptable carrier. If desired, further ingredients may be incorporated in the compositions, e.g. anti-inflammatory agents, disinfectant, antibiotics, etc.. Moreover, use may be made of wound-covers, e.g. plasters, bandages, dressings, gauze pads and the like, containing an appropriate wound healing composition. In particular use may be made of plasters, bandages, dressings, gauze pads and the like which have been impregnated or sprinkled with a liquid formulation containing the wound healing agent, e.g. with an aseptic aqueous solution, and used as such or, after evaporation of the liquid carrier, in dry form. Or said plasters bandages, dressings, aseptic gauzes and the like may have been strewn with a powdery solid composition or smeared, covered or coated with a semi-liquid composition. Preferred compositions for use in the method according to the present invention are creams.

The method of the present invention is applicable to either humans or animals. As wounds to be treated according to the present invention there may be mentioned all kinds of wounds caused intentionally or not intentionally, the latter being wounds caused, for example, by accidents of various kind, e.g. burning wounds, cutting wounds, puncture wounds, etc ..., the former being wounds caused by surgical operations, either by major or minor, human or veterinary surgery, also including transplantation wounds, e.g. wounds originating from skin transplantation. In particular, the method according to the present invention is useful in the treatment of burning wounds and bedsore wounds An advantage of the method of the present invention resides in the fact that, besides of having a beneficial effect on the healing process, there is also an effect on the infections often occuring during the healing process. wounds treated as in the method of this invention will be less subject or show an increased resistance to infections. Also, if they occur, infections will be less intense and can be overcome or healed more rapidly.

The method according to the present invention may be advantageously used in the treatment of ulcerating wounds and is particularly applicable in the treatment of chronic ulcerating wounds. The latter renders the present invention even more useful since up until now, there is no completely satisfying treatment of such wounds.

In a further aspect of the present invention, there is provided a wound-healing composition containing as active ingredient a serotonin-antagonistic compound, which preferably is a compound of formula (I) as defined hereinabove, and a wound acceptable carrier, and, if desired one or more further active ingredients such as disinfectants, antibiotics, anti-inflammatory agents and the like. Said wound-healing compositions can be prepared following methods generally employed in the art of pharmaceutical formulation, e.g., for preparing powders by thoroughly grinding and mixing the components; for solutions by dissolving the active ingredient in the liquid medium by shaking, stirring, if desirable, at higher temperatures; for semi-liquid formulations by dispersing the active ingredient in the semi-liquid carrier; and the like methods.

The following examples are intented to illustrate the scope of the present invention in all its aspects and not to delimit it thereto. As used in the following example Pluronic L 35 ® is a trademark for a block-copolymer containing polyoxyethylene and polyoxypropylene blocks.

A. COMPOSITION EXAMPLES

EXAMPLE 1

Placebo (formulation 1)

| | |
|---|---|
| propyleneglycol | 100.0 mg |
| hydroxypropylmethylcellulose | 15.5 mg |
| water | 884.5 mg |

The ingredients are mixed under intense stirring.

EXAMPLE 2

3-[2-[4-(4-fluorobenzoyl)-1-piperidinyl]ethyl]-2,4(1H,3H-quinazolinedione (ketanserin) 0.25% (formulation 2)

| | |
|---|---|
| 3-8 2-[4-(4-fluorobenzoyl)-1-piperidinyl]ethyl]-2,4(1H,3H-quinazolinedione tartrate | 3.46 mg |
| propyleneglycol | 99.0 mg |
| hydroxypropylmethylcellulose | 15.6 mg |
| water | 881.9 mg |

The active ingredient ketanserin tartrate is added to the water under vigorous stirring, whereupon the other ingredients are added.

EXAMPLE 3

3-[2-[4-(4-fluorobenzoyl)-1-piperidinyl]ethyl]-2,7-dimethyl-4H-pyrido[1,2-a]pyrimidin-4-one 0.25% (formulation 3)

| | |
|---|---|
| 3-[2-[4-(4-fluorobenzoyl)-1-piperidinyl]ethyl]-2,7-dimethyl 4H—pyrido[1,2-a]pyrimidin-4-one | 2.5 mg |
| propyleneglycol | 99.0 mg |
| hydroxypropylmethylcellulose | 15.6 mg |
| water | 881.9 mg |

EXAMPLE 4

| | |
|---|---|
| Ketanserin microfine | 2% |
| pluronic L 35 ® | 90.5% |
| Glycerol monostearate | 7.5% |

METHOD OF PREPARATION

Glycerol monostearate and Pluronic L 35 ® are introduced into a doublewall jacketed vessel and are heated to approximately 65° C. Stirring is applied until a homogeneous, clear liquid is obtained. This clear liquid is cooled to approximately 40° C., while gently stirring. Hereupon a slightly viscous, unctuous mass is formed. Subsequently, while homogenizing the mixture, ketanserin is sucked into the ointment by evacuating the vessel. Homogenizing is applied until ketanserin is evenly distributed in the ointment. The ointment is further cooled to 20°-25° C. while gently stirring.

EXAMPLE 5

| | |
|---|---|
| Ketanserin microfine | 2% |
| Polyethyleneglycol 400 | 78% |
| Polyethyleneglycol 4000 | 20% |

METHOD OF PREPARATION

Polyethyleneglycol 4000 and polyethyleneglycol 400 are introduced into a doublewall jacketed vessel and are heated to approximately 65° C. Stirring is applied until a homogeneous, clear liquid is obtained. This clear liquid is cooled to approximately 40° C., while gently stirring. Hereupon a slightly viscous, unctuous mass is formed. Subsequently, while homogenizing the mixture, ketanserin powder is sucked into the ointment by evacuating the vessel. Homogenizing is applied until ketanserin is evenly distributed in the ointment. The ointment is further cooled to 20°-25° C., while gently stirring.

B. PHARMACOLOGICAL EXAMPLES

The useful wound-healing properties of the serotonin-antagonistic compounds to be used in the method of the present invention can be demonstrated by the following experiments.

EXAMPLE 6

Materials and Methods

40 Male Wistar rats (mean body weight 150 g) were used. They were divided into four groups each consisting of 10 animals: control group, placebo group, formulation 2 group, and formulation 3 group. After eher anaesthesia, the flanks of the animals were clipped and disinfected. Wounds were made as follows: through a skinfold of the thoracic skin two circular skin flaps (1 cm diameter) were excised using a punch.

A once daily treatment was started one day after surgery. In all groups, wounds were dipped with a gauze pad soaked with a disinfectant. Thereafter either a dry gauze pad (control group) or a gauze pad dipped in the test formulation (formulations 1(placebo), 2 or 3) was then wrapped around the body and fixed with an adhesive tape. Blind scoring consisted of the recording of the presence or absence of complete healing of wounds 10 days after the start of the experiment.

Results

TABLE 1

| | Wound healing after 10 days | |
|---|---|---|
| Treatment group | No. of animals | No. of healed wounds vs. total |
| control | 10 | 5/20 |
| formulation 1 | 10 | 10/20 |
| formulation 2 | 10 | 15/20 |
| formulation 3 | 10 | 14/20 |

Significantly faster wound-healing was found for wounds treated with formulations 2 and 3 compared to control wounds and two placebo-treated wounds (formulation 1).

We claim:

1. A method of promoting wound-healing, which method comprises topically applying to the wound of an amount of a serotonin-antagonistic compound effective to promote wound-healing.

2. A method according to claim 1 wherein the serotonin-antagonist is selected from the group of compounds having the formula

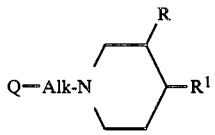  (I)

the pharmaceutically acceptable acid-addition salts thereof and the possible stereoisomeric forms thereof; wherein R is hydrogen or $C_{1-6}$alkyl;
Alk is $C_{1-4}$alkanediyl;
Q is a radical of formula

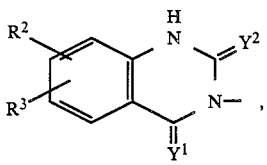  (a)

wherein
$Y^1$ and $Y^2$ are each independently O or S;
$R^2$ is hydrogen, halo, $C_{1-6}$alkyl, $C_{1-6}$alkyloxy, $CF_3$, $NO_2$, cyano, hydroxy, ($C_{1-10}$alkylcarbonyl)oxy, amino, mono- and di($C_{1-6}$alkyl)amino, ($C_{1-10}$-alkylcarbonyl)amino, phenylmethoxy or azido;
$R^3$ is hydrogen or halo; or
Q is a radical of formula

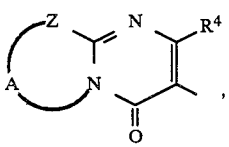  (b)

wherein
$R^4$ is hydrogen or $C_{1-6}$alkyl;
Z is $-S-$, $-CH_2-$ or $-CR^5=CR^6-$; said $R^5$ and $R^6$ being each independently hydrogen or $C_{1-6}$alkyl; and A is a bivalent radical $-CH_2-CH_2-$, $-CH_2-CH_2-CH_2-$ or $-CR^7=CR^8-$, said $R^7$ and $R^8$ being each independently hydrogen, halo, amino or $C_{1-6}$alkyl;
$R^1$ is a radical of formula —X—Ar (c), wherein
Ar is phenyl or substituted phenyl, said substituted phenyl bearing an amino group and/or 1, 2 or 3 halo atoms; and wherein X is

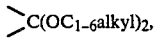

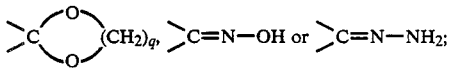

said $R^9$ being hydrogen or $C_{1-6}$ alkyl and
said q being the integer 2 or 3; or
$R^1$ is a radial of formula

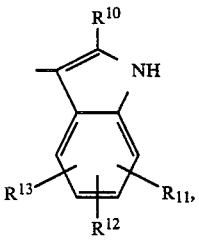  (d)

wherein
$R^{10}$ is hydrogen or $C_{1-6}$alkyl;
$R^{11}$, $R^{12}$ and $R^{13}$ are each independently hydrogen or halo; or
$R^1$ is a radical of formula

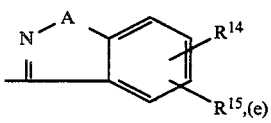  (e)

wherein
A is O or S;
$R^{14}$ and $R^{15}$ are each independently hydrogen, halo, hydroxy, $C_{1-6}$alkyloxy or $C_{1-6}$alkyl.

3. A method according to claim 2 wherein $R^1$ is a radical of formula (c).

4. A method according to claim 3 wherein Q is a radical of formula (a) wherein $Y^1$ and $Y^2$ are both oxygen atoms and $R^2$ and $R^3$ are both hydrogen; or wherein Q is a radical of formula (b), wherein $R^4$ is methyl, Z is $-CR^5=CR^6-$ wherein $R^5$ and $R^6$ are independently hydrogen or methyl, A is $-CR^7=CR^8-$ wherein $R^7$ and $R^8$ are independently hydrogen or methyl; and wherein in the radical (c) X is

and Ar is halo substituted phenyl.

5. A method according to claim 1 wherein the serotonin-antagonist is selected from the group consisting of 3-[2-[4-(4-fluorobenzoyl)-1-piperidinyl]ethyl]-2,4(1H,3H)-quinazolinedione which compound is generically designated as ketanserin, and 3-[2-[4-(4-fluorobenzoyl)-1-piperidinyl]ethyl]-2,7-dimethyl-4H-pyrido[1,2-a]pyrimidin-4-one.

6. A topical wound-healing composition comprising a wound-acceptable carrier and as an active ingredient an amount of a serotonin-antagonist compound effective to promote wound healing which composition is a cream, a jelly, a paste, an ointment, or a salve.

7. The composition of claim 6, wherein said serotonin-antagonist is selected from the group of compounds having the formula

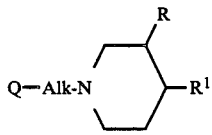 (I)

the pharmaceutically acceptable acid-addition salts thereof and the possible stereoisomeric forms thereof; wherein
R is hydrogen or $C_{1-6}$alkyl;
Alk is $C_{1-4}$alkanediyl;
Q is a radical of formula

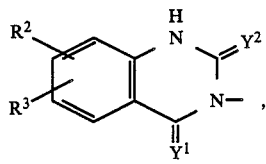 (a)

wherein
$Y^1$ and $Y^2$ are each independently O or S;
$R^2$ is hydrogen, halo, $C_{1-6}$alkyl, $C_{1-6}$alkyloxy, $CF_3$, $NO_2$, cyano, hydroxy, $(C_{1-10}$alkylcarbonyl)oxy, amino, mono- and di$(C_{1-6}$alkyl)amino, $(C_{1-10}$alkylcarbonyl)amino, phenylmethoxy or azido;
$R^3$ is hydrogen or halo; or
Q is a radical of formula

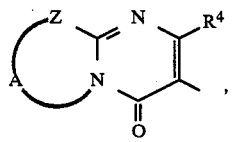 (b)

wherein
$R^4$ is hydrogen or $C_{1-6}$alkyl;
Z is —S—, —$CH_2$— or —$CR^5$=$CR^6$—; said $R^5$ and $R^6$ being each independently hydrogen or $C_{1-6}$alkyl; and A is a bivalent radical —$CH_2$—$CH_2$—, —$CH_2$—$CH_2$—$CH_2$— or —$CR^7$=$CR^8$—, said $R^7$ and $R^8$ being each independently hydrogen, halo, amino or $C_{1-6}$alkyl;
$R^1$ is a radical of formula —X—Ar (c), wherein
Ar is phenyl or substituted phenyl, said substituted phenyl bearing an amino group and/or 1, 2 or 3 halo atoms; and
wherein
X is

>C=O, >CH—OH, >CH—O—C(O)—$R^9$, >$CH_2$,

>C(O$C_{1-6}$alkyl)$_2$,

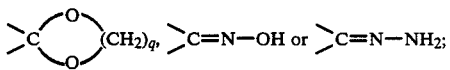

said $R^9$ being hydrogen or $C_{1-6}$ alkyl and
said q being the integer 2 or 3; or
$R^1$ is a radical of formula

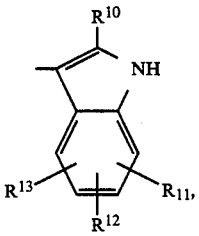 (d)

wherein
$R^{10}$ is hydrogen or $C_{1-6}$alkyl; $R^{11}$, $R^{12}$ and $R^{13}$ are each independently hydrogen or halo; or
$R^1$ is a radical of formula

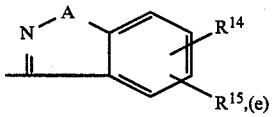 (e)

wherein
A is O or S;
$R^{14}$ and $R^{15}$ are each independently hydrogen, halo, hydroxy, $C_{1-6}$alkyloxy or $C_{1-6}$alkyl.

8. The composition according to claim 7, wherein $R^1$ is a radical of formula (c).

9. The composition according to claim 8, wherein Q is a radical of formula (a) wherein $Y^1$ and $Y^2$ are both oxygen atoms and $R^2$ and $R^3$ are both hydrogen; or wherein Q is a radical of formula (b), wherein $R^4$ is methyl, Z is —$CR^5$=$CR^6$— wherein $R^5$ and $R^6$ are independently hydrogen or methyl, A is —$CR^7$=$CR^8$— wherein $R^7$ and $R^8$ are independently hydrogen or methyl; and wherein in the radical (c) X is

>C=O and Ar is halo substituted phenyl.

10. The composition of claim 6, wherein the serotonin-antagonist is selected from the group consisting of 3-[2-[4-(4-fluorobenzoyl)-1-piperidinyl]ethyl]-2,4(1H,3H)-quinazolinedione which compound is generically designated as ketanserin, and 3-[2-[4-(4-fluorobenzoyl)-1-piperidinyl]ethyl]-2,7-dimethyl-4H-pyrido[1,2-a]pyrimidin-4-one.

11. A plaster, bandage, dressing or gauze pad wound-cover containing a topical wound healing semi-liquid composition comprising a wound-acceptable carrier and as an active ingredient an amount of a serotonin-antagonist compound effective to promote wound healing.

12. The wound-cover according to claim 11, which is a plaster, bandage, dressing or gauze pad impregnated or sprinkled with a liquid wound healing composition or strewn with a powdery solid wound-healing composition or smeared, covered or coated with a semi-liquid wound-healing composition.

13. The wound-cover according to claim 11, wherein the serotonin-antagonist is selected from the group of compounds having the formula

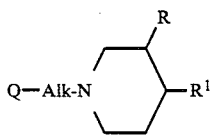 (I)

the pharmaceutically acceptable acid-addition salts thereof and the possible stereoisomeric forms thereof; wherein R is hydrogen or $C_{1-6}$alkyl;
Alk is $C_{1-4}$alkanediyl;
Q is a radical of formula

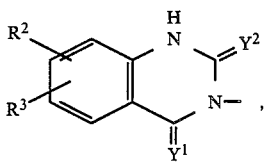 (a)

wherein
$Y^1$ and $Y^2$ are each independently O or S;
$R^2$ is hydrogen, halo, $C_{1-6}$alkyl, $C_{1-6}$alkyloxy, $CF_3$, $NO_2$, cyano, hydroxy, ($C_{1-10}$alkylcarbonyl)oxy, amino, mono- and di($C_{1-6}$alkyl)amino, ($C_{1-10}$alkylcarbonyl)amino, phenylmethoxy or azido;
$R^3$ is hydrogen or halo; or
Q is a radical of formula

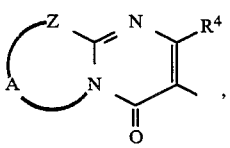 (b)

wherein
$R^4$ is hydrogen or $C_{1-6}$alkyl;
Z is —S—, —CH$_2$— or —CR$^5$=CR$^6$—; said $R^5$ and $R^6$ being each independently hydrogen or $C_{1-6}$alkyl; and A is a bivalent radical —CH$_2$—CH$_2$—, —CH$_2$—CH$_2$—CH$_2$— or —CR$^7$=CR$^8$—, said $R^7$ and $R^8$ being each independently hydrogen, halo, amino or $C_{1-6}$alkyl;
$R^1$ is a radical of formula —X—Ar (c), wherein
Ar is phenyl or substituted phenyl, said substituted phenyl bearing an amino group and/or 1, 2 or 3 halo atoms; and
wherein
X is $>$C=O, $>$CH—OH, $>$CH—O—C(O)—R$^9$, $>$CH$_2$, -continued $>$C(OC$_{1-6}$alkyl)$_2$,

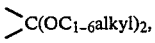 (CH$_2$)$_q$, $>$C=N—OH or $>$C=N—NH$_2$;

said $R^9$ being hydrogen or $C_{1-6}$ alkyl and
said q being the integer 2 or 3; or
$R^1$ is a radical of formula

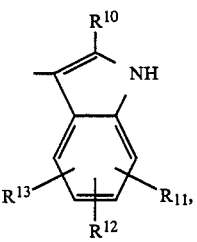 (d)

wherein
$R^{10}$ is hydrogen or $C_{1-6}$alkyl; $R^{11}$, $R^{12}$ and $R^{13}$ are each independently hydrogen or halo; or
$R^1$ is a radical of formula

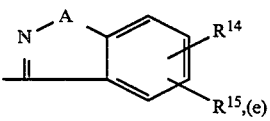 (e)

wherein
A is O or S; $R^{14}$ and $R^{15}$ are each independently hydrogen, halo, hydroxy, $C_{1-6}$alkyloxy or $C_{1-6}$alkyl.

14. The wound-cover according to claim 13, wherein $R^1$ is a radical of formula (c).

15. The wound-cover according to claim 14, wherein Q is a radical of formula (a) wherein $Y^1$ and $Y^2$ are both oxygen atoms and $R^2$ and $R^3$ are both hydrogen; or wherein Q is a radical of formula (b), wherein $R^4$ is methyl, Z is —CR$^5$=CR$^6$— wherein $R^5$ and $R^6$ are independently hydrogen or methyl, A is —CR$^7$=CR$^8$— wherein $R^7$ and $R^8$ are independently hydrogen or methyl; and wherein in the radical (c) X is $>$C=O and Ar is halo substituted phenyl.

16. The wound-cover according to claim 11, wherein the serotonin-antagonist is selected from the group consisting of 3-[2-[4-(4-fluorobenzoyl)-1-piperidinyl]ethyl]-2,4(1H, 3H)-quinazolinedione which compound is generically designated as ketanserin, and 3-[2-[4-(4-fluorobenzoyl)-1-piperidinyl]ethyl]-2,7-dimethyl-4H-pyrido[1,2-a]pyrimidin-4-one.

17. The wound-cover according to claim 11, wherein the wound-healing composition is a cream, a jelly, a paste, an ointment or a salve.

* * * * *